US011506606B2

(12) United States Patent
Bedell et al.

(10) Patent No.: US 11,506,606 B2
(45) Date of Patent: Nov. 22, 2022

(54) ALARM THRESHOLD ORGANIC AND MICROBIAL FLUORIMETER AND METHODS

(71) Applicant: SweetSense, Inc., Denver, CO (US)

(72) Inventors: Emily Bedell, Denver, CO (US); Katie Frankhauser, Denver, CO (US); Taylor Sharpe, Denver, CO (US); Daniel Wilson, Denver, CO (US); Evan Thomas, Denver, CO (US)

(73) Assignee: SWEETSENSE, INC., Denver, CO (US)

( * ) Notice: Subject to any disclaimer, the term of this patent is extended or adjusted under 35 U.S.C. 154(b) by 120 days.

(21) Appl. No.: 16/804,605

(22) Filed: Feb. 28, 2020

(65) Prior Publication Data
US 2020/0355612 A1    Nov. 12, 2020

Related U.S. Application Data

(63) Continuation-in-part of application No. 16/801,722, filed on Feb. 26, 2020.
(Continued)

(51) Int. Cl.
*G01N 21/64* (2006.01)
*G01N 33/18* (2006.01)
(Continued)

(52) U.S. Cl.
CPC ....... *G01N 21/6456* (2013.01); *G01N 21/643* (2013.01); *G01N 33/1826* (2013.01);
(Continued)

(58) Field of Classification Search
CPC ............ G01N 21/6456; G01N 21/643; G01N 33/1826; G01N 21/645; G01N 21/85;
(Continued)

(56) References Cited

U.S. PATENT DOCUMENTS

| 2007/0037135 A1* | 2/2007 | Barnes | G01N 21/31 435/4 |
| 2007/0257806 A1* | 11/2007 | Madden | G01N 33/18 340/603 |

(Continued)

FOREIGN PATENT DOCUMENTS

WO    WO-2018061015 A2 *    4/2018    ............. G01N 33/18

OTHER PUBLICATIONS

Edn, "When do you need a multichannel picoammeter?", Apr. 2013, AspenCore [online]. Retrieved from the Internet: <URL: edn.com/when-do-you-need-a-multichannel-picoammeter> (Year: 2013).*

(Continued)

*Primary Examiner* — Jill A Warden
*Assistant Examiner* — Henry H Nguyen
(74) *Attorney, Agent, or Firm* — K&L Gates LLP

(57) ABSTRACT

In-situ fluorimeters and methods and systems for collecting and analyzing sensor data to predict water source contamination are provided. In one embodiment, a method is provided that includes receiving sensor data regarding a water source. Changepoints may then be calculated within the sensor data and the sensor data may be split into intervals at the changepoints. A machine learning model may then be used to classify the intervals and a predicted contamination event for the water source may be identified based on the classified intervals. In another embodiment, an in-situ fluorimeter is provided. The in-situ fluorimeter comprises one or more UV LEDs centered around a pre-set excitation wavelength (e.g., a TLF excitation wavelength), a bandpass filter, a lens, a photodiode system, a machine learning platform; and an alarm triggered by contamination events, wherein the alarm is calibrated through the machine learning system.

12 Claims, 9 Drawing Sheets

Related U.S. Application Data

(60) Provisional application No. 62/843,860, filed on May 6, 2019, provisional application No. 62/843,836, filed on May 6, 2019.

(51) Int. Cl.
*G06N 20/00* (2019.01)
*G05B 13/00* (2006.01)
*G06N 5/04* (2006.01)
*G01N 21/85* (2006.01)
*G08B 21/18* (2006.01)
*G08B 29/26* (2006.01)

(52) U.S. Cl.
CPC .............. *G05B 13/00* (2013.01); *G06N 5/04* (2013.01); *G06N 20/00* (2019.01); *G08B 21/18* (2013.01); *G08B 29/26* (2013.01); *G01N 21/645* (2013.01); *G01N 21/85* (2013.01); *G01N 2021/6467* (2013.01); *G01N 2201/062* (2013.01); *G01N 2201/0626* (2013.01); *G01N 2201/126* (2013.01)

(58) Field of Classification Search
CPC ....... G01N 2201/062; G01N 2201/126; G01N 2021/6467; G01N 2201/0626; G01N 21/6486; G06N 5/04; G06N 20/00; G05B 13/00; G08B 29/26; G08B 21/18
See application file for complete search history.

(56) References Cited

U.S. PATENT DOCUMENTS

| 2016/0202228 | A1* | 7/2016 | Ba | G01N 33/182 |
| | | | | 702/50 |
| 2017/0038301 | A1* | 2/2017 | Flanagan | G01N 33/1886 |
| 2017/0139078 | A1* | 5/2017 | Knight | G06N 20/10 |
| 2017/0290515 | A1* | 10/2017 | Butte | G01N 21/645 |
| 2018/0055495 | A1* | 3/2018 | Tehrani | A61B 8/12 |
| 2018/0299375 | A1* | 10/2018 | Young | G01N 33/2888 |
| 2020/0311557 | A1* | 10/2020 | Jin | G06N 3/0454 |

OTHER PUBLICATIONS

Arnon et al., "Water characterization and early contamination detection in highly varying stochastic background water, based on Machine Learning methodology for processing real-time UV-Spectrophotometry", Feb. 2019, Water Research, 155, 333-342 (Year: 2019).*

* cited by examiner

| Concentration [ppb] | Oscilloscope [mV] | Multimeter [mV] | Arduino [mV] |
|---|---|---|---|
| 0 | 145 | 149 | 116.60 |
| 1 | 257 | 255 | 203.92 |
| 3 | 575 | 550 | 383.52 |
| 10 | 801 | 770 | 611.05 |
| 100 | 1543 | 1444 | 1050.30 |

FIG. 4

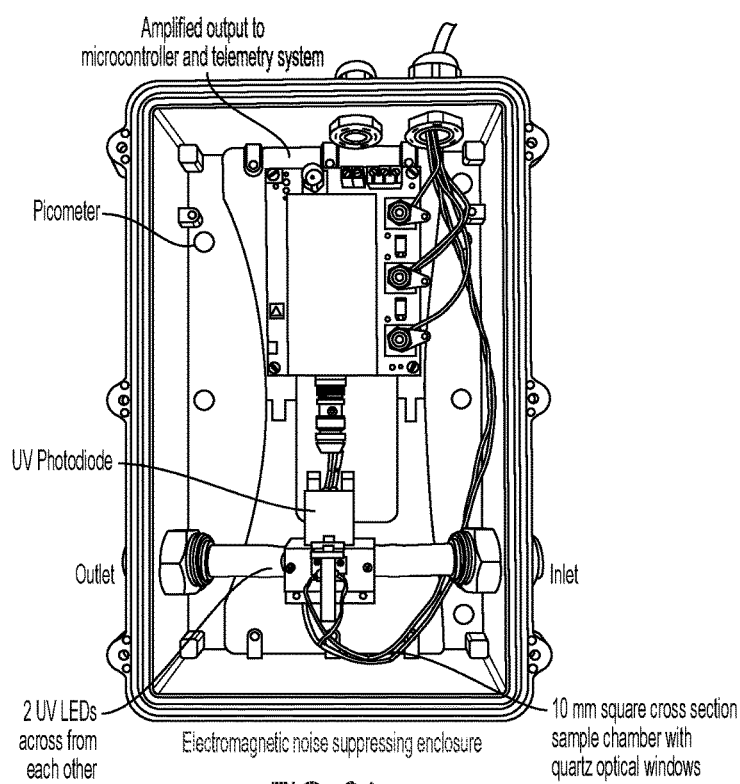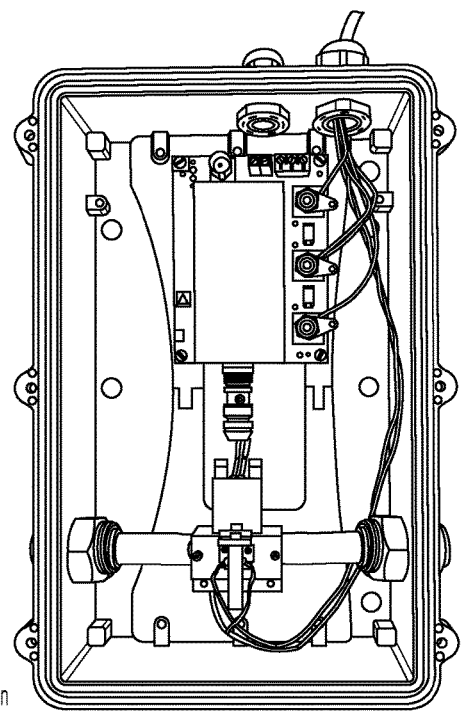
FIG. 9A
FIG. 9B

ALARM THRESHOLD ORGANIC AND MICROBIAL FLUORIMETER AND METHODS

CROSS-REFERENCE TO RELATED APPLICATIONS

The present application claims priority to U.S. Provisional Patent Application No. 62/843,860, entitled "ALARM THRESHOLD MICROBIAL FLUORIMETER AND METHODS" and filed on May 6, 2019, and claims priority to U.S. Provisional Patent Application No. 62/843,836, entitled "MACHINE LEARNING TECHNIQUES FOR IMPROVED WATER SERVICE DELIVERY" and filed on May 6, 2019, and also a continuation-in-part of U.S. patent application Ser. No. 16/801,722, entitled "MACHINE LEARNING TECHNIQUES FOR IMPROVED WATER SERVICE DELIVERY" and filed on Feb. 26, 2020 the disclosure of which are incorporated herein by reference for all purposes.

GOVERNMENT PATENT RIGHTS STATEMENT

This invention was made with Government support under Grant No. 1738321 awarded by the National Science Foundation. The Government has certain rights in this invention.

BACKGROUND

Access to safe, clean drinking water sources is a fundamental human need, and in, many parts of the world, access to these safe, clean, sources remains a challenge. In order to assess whether a water source is safe and clean, testing and monitoring must occur.

The World Health Organization Guidelines for Drinking Water Quality require water service providers to test that the water is safe, i.e., lacking in dangerous contaminants. Compliance requires organic contaminant, including microbial, water quality testing. This testing often occurs infrequently in emerging markets due to various obstacles such as cost, lack of equipment, and a lack of trained personnel.

The current products available for testing are expensive and imprecise. For example, there are three types of available products to test for *E. coli* (an indicator of fecal contamination in the water source): (1) Presence-Absence (PA); (2) Most Probably Number (MPN); and (3) Colony Counting (CN). These cost between 50 cents and $5.00 per sample, excluding personnel and logistics costs.

These tests require 16-24 hours to complete, making it practically impossible to detect a contamination event prior to the affected water reaching consumers.

While there are electronic in-situ sensors available off the shelf for monitoring water quality parameters like pH, turbidity and chlorine, at present, there are no viable in-situ electronic sensors for monitoring organic and/or microbial contamination of drinking water. Further, the electronic in-situ sensors currently available require frequent cleaning, are not intended for long term autonomous operation, and cost $7,500 or more.

Accordingly, there is a need for an in-situ organic and/or microbial sensor capable of autonomous, affordable, long term use.

SUMMARY

The present disclosure presents new and innovative organic and/or microbial fluorimeters or fluorescent spectrometers capable of being used in-situ for long-term autonomous use and systems and methods for their use.

Throughout the disclosure, a tryptophan-like fluorescence (TLF) is used as a non-limiting, exemplary fluorescent target for the fluorimeters or spectrometers. The fluorimeters or spectrometers and the related systems of the present disclosure may also be used to detect any other substance of contaminations comprising at least one fluorophore. For example, the fluorimeters or spectrometers and the related systems of the present disclosure may be used to detect any organic substance, biological and/or microbial comprising at least one fluorophore.

In one aspect, an in-situ fluorimeter or fluorescent spectrometer is provided. The in-situ fluorimeter comprises of one or more ultraviolet light emitting diodes (UV LEDs) centered around an excitation wavelength, a bandpass filter centered around a pre-set excitation wavelength, a lens, a photodiode system, a machine learning platform; and an alarm triggered by contamination events, wherein the alarm is calibrated through the machine learning system.

In one aspect, the bandpass filter is centered around a TLF excitation wavelength.

In one aspect, the one or more UV LEDs are centered around a TLF excitation wavelength.

In another aspect, the one or more UV LED are centered around an excitation wavelength for an organic contaminant selected from the group consisting of microbes, algaes, fertilizers, resins, phenols, colorants, alcohols, aldehydes, and biowastes.

In one aspect, the in-situ fluorimeter further comprises a picometer.

In one aspect, the in-situ fluorimeter further comprises a microcontroller.

In one aspect, the microcontroller comprises: a processor; and a memory storing instructions which, when executed by the processor, cause the processor to: receive sensor data regarding a water fixture; calculate changepoints within the sensor data; split the sensor data into intervals at the changepoints; classify the intervals using a machine learning model; and identify a predicted contamination of the water source based on the classified intervals.

In one aspect, the sensor data is associated with a plurality of water fixtures, and wherein identifying a predicted contamination includes identifying a predicted contamination for at least a subset of the plurality of water fixtures.

In one aspect, a plurality of the in-situ fluorimeters constitute a group of sensors, which are configured in such a way that the sensor data from the group of sensors, when analyzed, helps improve a single sensor's estimate.

In another aspect, a system for monitoring a microbial level in-situ in a water source is provided. The system comprises: a fluorimeter comprising: one or more UV LEDs centered around an excitation wavelength; a bandpass filter; a lens; and a photodiode system; a machine learning platform; and, an alarm triggered by contamination events, wherein the alarm is calibrated through the machine learning system.

In one aspect, the fluorimeter further comprises a picometer.

In one aspect, the fluorimeter further comprises an enclosure to suppress electromagnetic noise.

In one aspect, the one or more UV LEDs are centered around a TLF excitation wavelength.

In one aspect, the one or more UV LEDs are centered around an excitation wavelength for an organic contaminant selected from the group consisting of microbes, algaes, fertilizers, resins, phenols, colorants, alcohols, aldehydes, and biowastes.

In one aspect, the system further comprises a microcontroller.

In one aspect, the microcontroller comprises: a processor; and a memory storing instructions which, when executed by the processor, cause the processor to: receive sensor data regarding a water fixture; calculate changepoints within the sensor data; split the sensor data into intervals at the changepoints; classify the intervals using a machine learning model; and identify a predicted contamination of the water source based on the classified intervals.

In one aspect, the sensor data is associated with a plurality of water fixtures, and identifying a predicted contamination includes identifying a predicted contamination for at least a subset of the plurality of water fixtures.

In another aspect, a method to predict water contamination and set off an alarm to prevent distribution of contaminated water is provided that includes receiving sensor data regarding a water source. Changepoints may then be calculated within the sensor data and the sensor data may be split into intervals at the changepoints. A machine learning model may then be used to classify the interval and a predicted contamination event for the water source may be identified based on the classified intervals.

In one aspect, the contamination of the water source includes one or more of an organic contaminant selected from the group consisting of microbes, algaes, fertilizers, resins, phenols, colorants, alcohols, aldehydes, and biowastes.

In one aspect, calculating the changepoints includes: calculating a first z-score for a first segment of the sensor data and a second z-score for a second segment of the sensor data; determining that a difference between the first and second z-scores exceeds a predetermined threshold; and identifying a changepoint between the first segment and the second segment.

In one aspect, the predetermined threshold may be remotely updated.

In one aspect, the sensor data is associated with a plurality of water fixtures, and identifying a predicted contamination includes identifying a predicted contamination for at least a subset of the plurality of water fixtures.

The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

FIG. 4 illustrates data (as Arduino, used for logging data from an exemplary embodiment of the present disclosure) from challenges to an example embodiment of the presently disclosed system showing the ability to detect 1 ppb TLF, a high risk microbial contamination.

FIG. 9A illustrates an annotated version a fluorimeter installed with an electromagnetic noise suppressing enclosure according to an exemplary embodiment of the present disclosure.

FIG. 9B illustrates a non-labeled version a fluorimeter installed with an electromagnetic noise suppressing enclosure according to an exemplary embodiment of the present disclosure.

DETAILED DESCRIPTION OF EXAMPLE EMBODIMENTS

Figure 1:
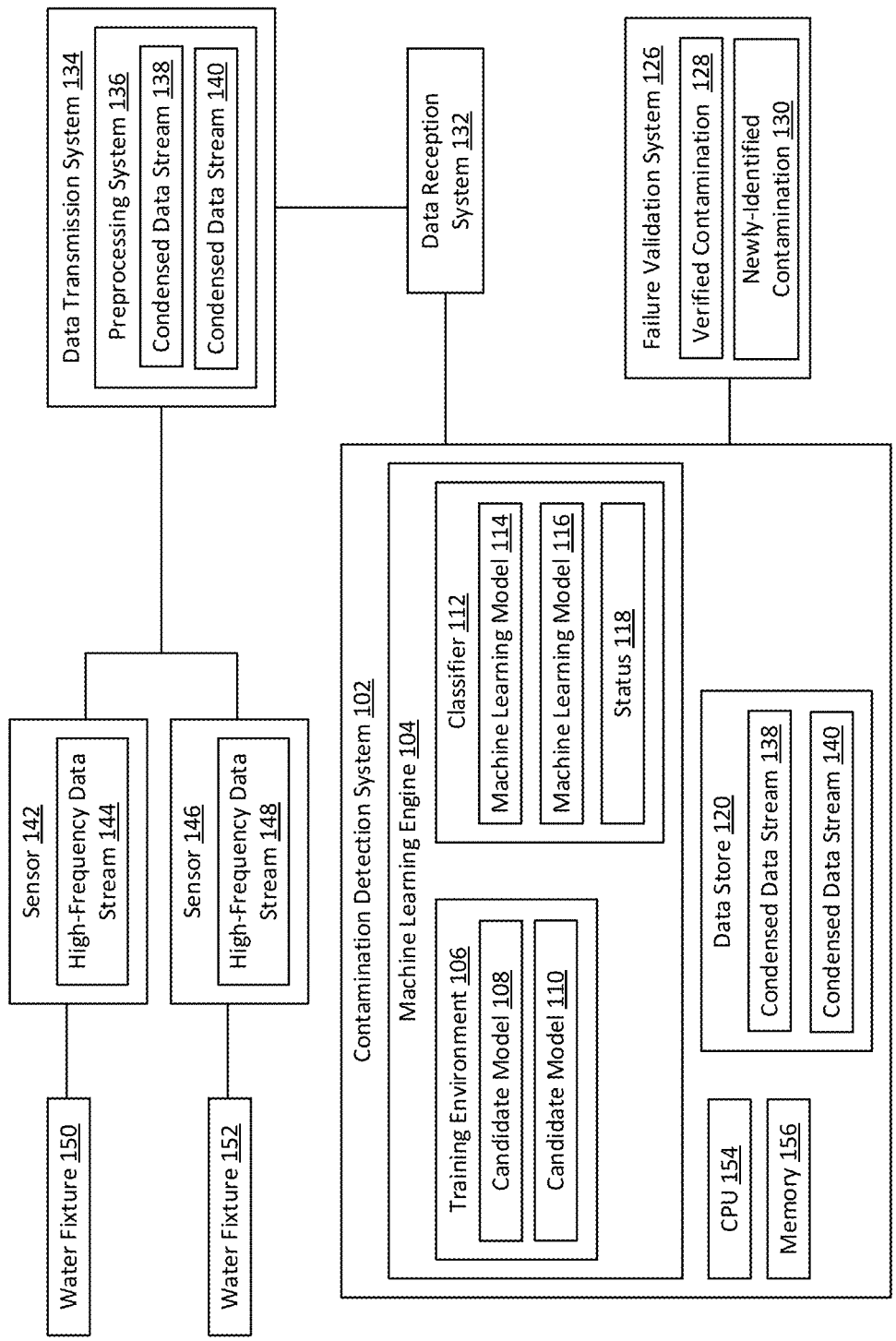
FIG. 1 illustrates a system according to an exemplary embodiment of the present disclosure.

Laboratory grade optical fluorimeters can be used to measure real time in-situ fecal or other contamination by detecting fluorescence such as tryptophan fluorescence (TLF) associated with the presence of microbial contamination, such as *E. coli*. However, these sensors are very expensive, costing $7,500 or more per sensor, require frequent cleaning and are not intended for long term autonomous operation. Biofouling and baseline drift attenuate and ambiguate the signal, rendering the sensors ineffective or useless.

Because of the remote nature of many water sources, it is often difficult for technicians to access the sites and detectors that require regular cleaning and maintenance are impractical. To be effective, a microbial sensor for these water sources requires the ability to be used in situ autonomously for long periods of time, without compromised performance.

In contrast, a sensor or detector according to the present disclosure may be installed in-situ without these obstacles. In an embodiment, the sensor comprises low-cost, robust hardware. The sensor may comprise semiconductor technologies with one or more UV LED centered around a pre-set excitation wavelength. In one embodiment, the pre-set excitation wavelength is a TLF excitation wavelength. The sensors may also comprise a bandpass filter, lens, and a photodiode system in line to detect changing emission intensity of fluorescence such as TLF or another excitation wavelength in the water supply. In an embodiment, this apparatus may be combined with a picometer, which is defined as a device for signal detection and logging with a microcontroller.

The hardware may be paired with machine learning to characterize in-situ water quality over the long term and identify potential organic, including microbial, contamination through alarm-based event detection.

The sensor of the present disclosure is able to avoid operational issues from microbial and mineral fouling over time. This fouling can lead to baseline drift in fluorimeter output. For example, mineral fouling on the detector's window that blocks transmission of a fluoresced light will reduce the total signal measured by the detector. Similarly, a biofilm that develops on the emitter's window will fluoresce, and may scatter light into the detector, giving a falsely high reading. Added to both of these baseline drift problems is the issue of noise in the emitter and detector. Detecting a pulse in organic contaminants, including water-borne microbes, against this background of noise and baseline drift is a significant challenge.

Sophisticated machine learning techniques in combination with the production of high-stability output circuits and low-noise amplification circuits can address this issue. In order to inform the generation of initial machine learning algorithms, it is necessary to examine biofouling trends, as well as baseline drift in emitters and detectors, along with the effects of temperature and turbidity.

The sensor of the present disclosure may be used in emerging economies as it is compatible with a wide variety of water distribution infrastructures. It may be used in resource and power constrained environments.

In an embodiment, the sensor may be calibrated through site-sensor specific baseline calibration. Sudden and large changes in fluorescence such as TLF will be able to be detected. A universal threshold would not need to be used for all sensors.

In an embodiment, the sensor is a detector.
In an embodiment the sensor is a fluorimeter.
In an embodiment, the sensor detects TLF.
In another embodiment, the sensor detects other fluorescence.
In an embodiment, the sensor detects multiple types of fluorescence.

In an embodiment, the sensor may be used to detect organic contaminants such as microbes, algaes, fertilizers, resins, phenols, colorants, alcohols, aldehydes, and biowastes. In one embodiment, the sensor may be used to detect organic contaminants such as dye, humic substances (such as humic acid, fulvic acid, or humin, which result from the decay of organic matter and pharmaceuticals such as antibiotics), phenolic compounds, petroleum, surfactants, pesticides, and pharmaceuticals.

The sensor of the present disclosure can keep a running log of the baseline and off-nominal fluorescence (such as TLF) features of the water source. The sensor is then able to trigger an alarm through internet, cellular, radio, satellite, or other similar channels in the event of a sudden increase in the fluorescence (such as TLF). The sensor of the present disclosure is capable of detecting and responding to sudden changes in water quality.

These sensors may be configured to remotely provide data regarding the water fixtures to a monitoring platform, for example via cellular and/or satellite networks. However, such sensors may produce a vast amount of data, necessitating automated review to timely detect issues with the water quality. A machine learning platform trained on such sensor data may assist with building and refining one or more machine learning models capable of rapid analysis of sensor data to identify water quality conditions. Based on this analysis, the models may also identify when a contamination event has occurred.

This analysis may involve several steps. First, contamination events may be identified from raw sensor data. Second, the identified events may be verified by field technicians when they visit the deployment site. Third, predictive models may then be generated that will predict incidences of contamination, allowing distribution of water to be stopped before populations consume the contaminated water.

FIG. 1 depicts a system 100 according to an exemplary embodiment of the present disclosure. The system 100 may be used to capture, collect, and classify sensor data from water fixtures to predict water contamination. The system 100 includes a contamination detection system 102, a data transmission system 134, a data reception system 132, and sensors 142, 146 connected to respective water fixtures 150, 152. The system may include a failure validation system 126.

The sensors 142, 146 may be configured to capture high-frequency data streams 144, 148 from their respective water fixtures 150, 152. For example, the water fixtures 150, 152 may include one or more of a pump, faucet, borehole, pipe, water tank, and bacterial sensor. The sensors 142, 146 may be configured to capture operational data from these water fixtures 150, 152. For example, in additional to the sensor capable of detecting microbial contamination, the sensors 142, 146 may include one or more of a current sensor, a flow rate sensor, a fill level sensor, and a motion sensor. The sensors 142, 146 may accordingly capture information regarding when the water fixtures 150, 152 are used, as well as information regarding how much water is used in addition to whether a contamination event has occurred. The sensors 142, 146 may capture data at regular intervals (e.g., every second, every minute, every five minutes), forming the high-frequency data stream 144, 148.

The data transmission system 134 may be configured to receive the high-frequency data streams 144, 148 generated by the sensors 142, 146 and to transmit such data to the contamination detection system 102 via the data reception system 132. In certain implementations, the data transmission system 134 may transmit the data to the data reception system 132 via satellite data transmission. In particular, such deployments may be necessary or advantageous in areas with poor cellular data coverage. In other implementations, alternative transmission techniques may be used (e.g., cellular data, Ethernet, Wi-Fi connections). Because data may be more expensive to transfer via satellite data transmission (e.g., 2-3 times more expensive than cellular data transmissions), implementations relying on satellite data transmission may be configured to reduce the size of the high-frequency data streams 144, 148 prior to transmission. Accordingly, the data transmission system 134 may include a preprocessing system 136 configured to generate condensed data streams 138, 140 based on the high-frequency data streams 144, 148. For example, to reduce the size of the high-frequency data stream 144, 148, the preprocessing system 136 may average one or more data points from the high-frequency data stream 144, 148 into a single data point of the condensed data stream 130, 140. For example, the preprocessing system 136 may be configured to average data points captured during a certain time interval (e.g., every 10 minutes, every 30 minutes, every hour), to count the number of hours in a time period (e.g., a day) with water fixture 150, 152 usage, and/or to generate a binary indicator of whether the water fixture 150, 152 detected a contamination event as indicated via fluorescence (such as TLF) level.

Figure 2:
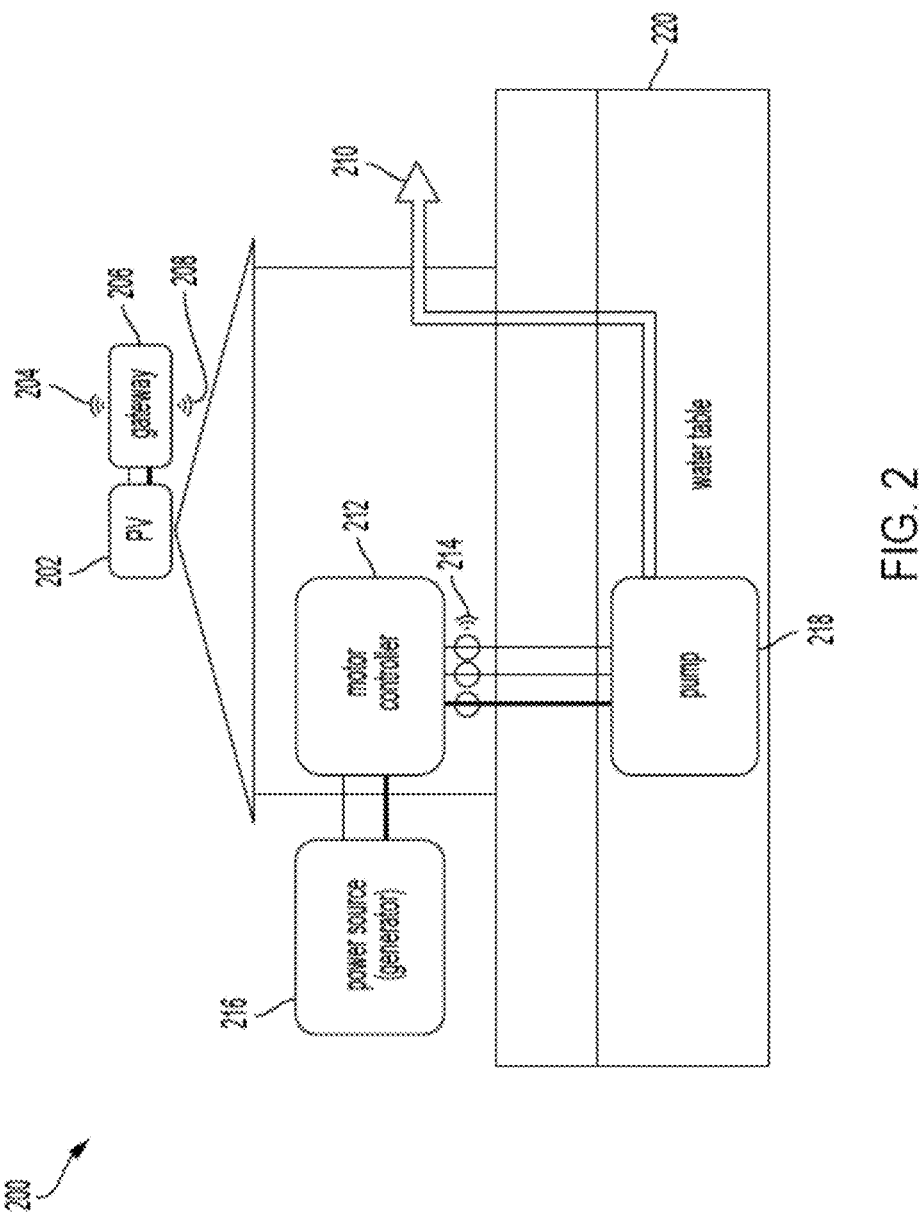
FIG. 2 illustrates a sensor deployment according to an exemplary embodiment of the present disclosure.

FIG. 2 depicts a sensor deployment 200 according to an exemplary embodiment of the present disclosure. For example, the sensor deployment 200 may depict an implementation of the water fixtures 150, 152, the sensors 142, 146, and the data transmission system 134. The sensor deployment 200 includes a pump 218 configured to pump water out of a water table 220 to an output 210. The pump 218 is controlled by a motor controller 212 and powered from a power source 216 (e.g., a generator) via the motor controller 212. The sensor deployment 200 includes one or more sensors 214 connected to the power leads between the motor controller 212 and the pump 218. In certain implementations, the sensors 214 may be provided as part of the pump 218. The sensor deployment 200 also includes a gateway 206 powered by photovoltaic array 202. The gateway 206 includes a receiver 208 configured to receive data from the sensors 214 via wireless transmission and a transmitter 204 configured to transmit data for further processing. The gateway 206 may implement one or more features of the data transmission system 134, including the preprocessing system 136. In other implementations, the sensors 214 may implement the preprocessing system 136, e.g., to save wireless bandwidth between the sensors 214 and the receiver 208.

Returning to FIG. 1, the contamination detection system 102 may receive data from the data transmission system 134 via the data reception system 132. In implementations where the data transmission system 134 is implemented using satellite data transmissions, the data reception system 132 may receive the satellite data transmissions and may relay them to the contamination detection system 102 via terrestrial data transmission means (e.g., Ethernet, cellular data, wireless networking/Wi-Fi). The contamination detection system 102 may then store the received condensed data streams 138, 140 in the data store 120.

The contamination detection system 102 may be configured to analyze condensed data streams 138, 140 stored in the data store 120 to predict contamination events. For example, the machine learning engine 104 may be configured to analyze the condensed data streams 130, 140 with a classifier 112 to identify predicted contamination events 118. The classifier 112 may utilize one or more machine learning models 114, 116 in performing the analysis. Additionally, to increase detection accuracy, the machine learning engine 104 may also include a training environment 106 configured to train the classifier 112. The training environment 106 includes a plurality of candidate models 108, 110 that may be tested and refined using training data to enhance the machine learning models 114, 116. In particular, the classifier 112 may comprise a collection of machine learning models 114, 116 that were each developed and refined as candidate models 108, 110 prior to being deployed within the classifier 112.

The system 100 further includes a contamination validation system 126, which may be configured to verify predicted contamination events 118 from the contamination detection system 102. For example, the contamination validation system 126 may be configured to receive user input from technicians in the field, who visit and inspect water fixtures 150, 152 that have been identified via an alarm as having a contamination event occur. If the technician is able to verify a contamination event, the technician may generate a verified contamination event 128. The verified contamination event 128 may indicate that the predicted contamination 118 did occur. In addition, if the technician notices a contamination event at a water fixture 150, 152 that has no corresponding predicted contamination 118 (e.g., during routine maintenance and monitoring), the technician may create a newly-identified contamination 130 via the contamination validation system 126. In certain implementations, the contamination validation system 126 may be implemented at least in part by a software application running on a mobile device (e.g., a computerized form accessible via a smart phone or other portable computing device).

The contamination system 102 also includes a CPU 154 and a memory 156. The CPU 154 and the memory 156 may implement one or more aspects of the contamination system 102, such as the machine learning engine 104 and the data store 120. For example, the memory 156 may store instructions which, when executed by the CPU 154 may perform one or more of the operational features of the contamination system 102. In addition, although not depicted, the sensors 142, 146, the data transmission system 134, the data reception system and/or the failure validation system 126 may also include a CPU and memory responsible for implementing one or more features.

The system may further implement a classifying system. The classifying system may be an example implementation of the classifier 112. The classifier 112 includes a data stream splitter and an interval classifier. The data stream splitter receives a condensed data stream and the interval classifier receives data such as biofouling trends, as well as baseline drift in emitters and detectors, along with the effects of temperature and turbidity. Using the data stream splitter and the interval classifier, the classifier 112 identifies the predicted contamination.

The data stream splitter may be configured to split the condensed data stream into a plurality of data stream intervals. As explained further below, the data stream splitter may split the condensed data stream 140 using a changepoint algorithm.

The interval classifier may then analyze each of the data stream intervals to assign a classification for each data stream intervals. For example, the machine learning models 114, 116 may analyze sensor data from the data stream intervals and may each generate an estimated classification for the data stream intervals. The interval classifier may then combine the estimated classifications (e.g., using one or more weights associated with each machine learning model 114, 116) to generate a classification for the data stream intervals. The interval classifier may be configured to assign classifications to each data stream interval based on the type of contamination seeking to be detected.

The machine learning models 114, 116 may be trained in the training environment 106 of the machine learning engine 104.

In identifying behavior, the machine learning models 114, 116 may utilize multiple features. For example, in order to generate the initial machine learning algorithms, biofouling trends, baseline drift in emitters and detectors, and the effects of temperature and turbidity or combinations thereof may be used.

In an embodiment, the machine learning platform uses z-score corrected fluorescence readings to adapt to diurnal and seasonal changes in water turbidity and baseline contamination. Additionally, this learner self-corrects for the sensor's baseline drift in the sensor, allowing for adaptation to light sensor fouling and degradation over time.

In an embodiment, the raw data from the sensor is transmitted to the machine learning platform daily. The platform generates dirty water alarms informed by threshold coefficient calculated by the machine learner. Each night, the learner updates the sensor with proper coefficients threshold readings for that day's dirty water alarms. The simple on-sensor algorithm is able to predict if the water is contaminated and send data to the backend in the case that an alarm threshold is breached.

Once trained, the machine learning models 114, 116 may analyze the defined features on a continual basis and may generate a regular statistic (e.g., a day-wise statistic) that estimates the likelihood of a contamination event at a particular site compared to a certain training set of data that is indicative of either contaminated or uncontaminated readings. For example, the regular statistic may be generated by classifying the data stream intervals from the condensed data stream 140 (e.g., the condensed data stream 140 from the preceding day). In certain implementations, the training environment 106 may be implemented at least in part by the SuperLearner platform and may use cross-validation to select the machine learning models 114, 116 as an optimal combination of the candidate models 108, 110. The candidate models 108, 110 may include models of different types. Although only two machine learning models 114, 116 are depicted, in one implementation, the machine learning models 114, 116, may be implemented from models including a random forest model, a lasso model, an extreme gradient boosting (xgboost) model, and a mean proportion model. A weighted combination of these models may be selected to maximize the cross-validated multinomial log likelihood of correctly identifying failure in a training dataset.

For example, training data may be labeled based on previously-collected sensor data. Labels may be manually applied using a combination of field-verified pump statuses (e.g., via the contamination validation system 126) and historical knowledge of patterns of fixture performance (e.g., based on the historical water quality data).

One or more of the machine learning models 114, 116 may also incorporate other external data, such as temperature and turbidity.

Figure 7:
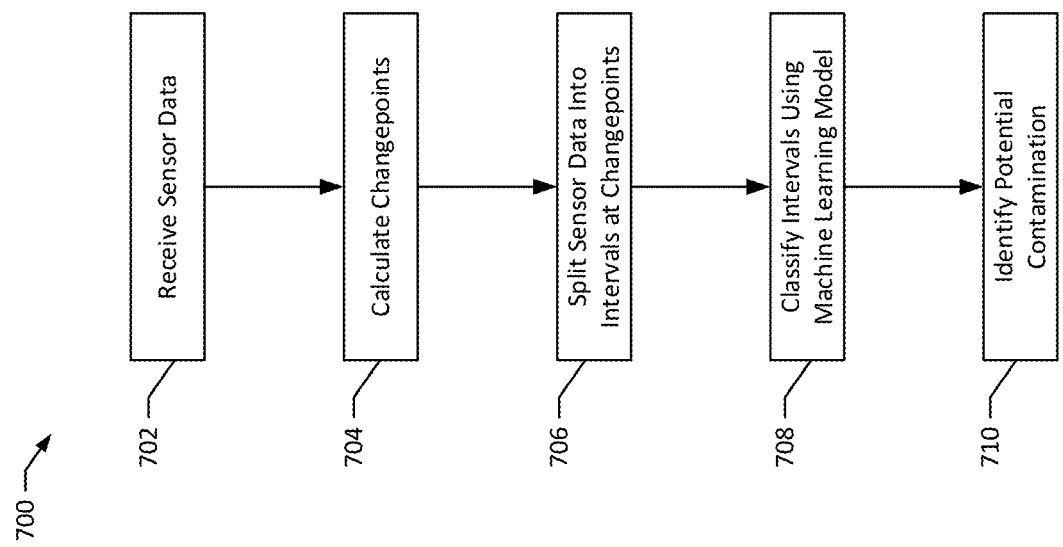
FIG. 7 illustrates a method according to an exemplary embodiment of the present disclosure.

FIG. 7 depicts a method 700 according to an exemplary embodiment of the present disclosure. The method 700 may be performed to analyze sensor data from water fixtures 150, 152 to identify predicted contamination events 118 in the water sources. The method 700 may be implemented on a computer system, such as the system 100. For example, the method 700 may be performed by the contamination system 102, such as by the classifier 112. The method 700 may also be implemented by a set of instructions stored on a computer readable medium that, when executed by a processor, cause the processor to perform the method. For example, all or part of the method 700 may be implemented by the CPU 154 and the memory 156. Although the examples below are described with reference to the flowchart illustrated in FIG. 7, many other methods of performing the acts associated with FIG. 7 may be used. For example, the order of some of the blocks may be changed, certain blocks may be combined with other blocks, one or more of the blocks may be repeated, and some of the blocks described may be optional.

The method 700 begins with the classifier 112 receiving sensor data (block 702). For example, the classifier 112 may receive a condensed data stream 138, 140 generated from the high-frequency data stream 144, 148 of a sensor 142, 146. In particular, the sensor data may represent water quality characteristics over time for a one or more site.

The classifier 112 may then calculate changepoints within the received sensor data (block 704). For example, the classifier 112 may use a changepoint detection technique that uses two sample z-tests to compare adjacent periods of time to test for a prospective changepoint. In particular, such a test may be used to compare data stream intervals indicating historical water quality and data stream intervals involving a binary indicator of TLF flare or no flare. For example, a prospective changepoint may be detected if a difference between two z-tests for adjacent periods of time exceeds a predetermined threshold. As a specific example, if the difference between two z-scores exceeds 3, a changepoint may be identified, indicating a change in usage patterns. Changepoints may also be created before and after any contamination event or a historical fluorescence (such as TLF) reading. In certain implementations, the predetermined threshold may be updated automatically (e.g., based on verified changepoints) and/or may be updated remotely via communication with the data transmission system 134 (e.g., via the status detection system 102). In particular, in certain instances, the predetermined threshold may be updated based on a region-wide analysis of sensor data from multiple sites located in the same region (e.g., accessing the same water table).

The classifier 112 may then split the sensor data into intervals at the changepoints (block 706). For example, the classifier 112 may split the condensed data stream 140 into a plurality of data stream intervals at the identified changepoints. For instance, the classifier 112 may split the condensed data stream 140 into the data stream intervals without overlapping data points between the data stream intervals. In other implementations, the data stream intervals may be split with overlapping data points between the intervals.

The classifier 112 may then classify the data stream intervals using at least one machine learning model 114, 116 (block 708). As explained above, the machine learning model 114, 116 may analyze each data stream interval and may generate a classification for each data stream interval. In particular, the machine learning model 114, 116 may be trained to analyze the data stream intervals. The interval classifier 404 may analyze and classify each data stream interval independently, or may analyze and classify more than one data stream interval in parallel. As further explained above, the interval classifier and/or the machine learning model 114, 116 may also incorporate temperature and turbidity data into the analysis of the data stream intervals (e.g., by adjusting the analysis and/or the data points within the data stream intervals to account for weather related water conditions such as temperature and turbidity). In still further implementations, the classifier 112 may incorporate data stream intervals corresponding to multiple water fixtures 150, 152. For example, the classifier 112 may be configured to analyze and classify data stream intervals from water fixtures that are located near one another. In certain implementations, the data stream intervals from multiple water fixtures may be analyzed to classify data stream intervals associated with a particular site. In such implementations, classifying data stream intervals based on sensor data from multiple water fixtures may improve the accuracy of the classification for the individual site. For example, if there are five water fixtures located in a particular region and drawing from the same water table, and three of the five water fixtures have data stream intervals classified as a potential contamination, data stream intervals from the other two water fixtures may be more likely to be classified as a potential contamination (e.g., as a result of a contamination in the water table).

The classifier 112 may then identify a predicted contamination event 118 (block 710). For example, based on the classifications, the classifier 112 may identify a predicted contamination event 118 if more than one of the data stream intervals receive a classification indicating contamination. The classifier 112 may then generate the predicted contamination event 118 to identify the water fixture 150, 152 at the water source associated with the condensed data stream 140 from which the data stream interval originated.

Once a predicted contamination event 118 is identified, an alarm may be triggered to prevent distribution of the contaminated water to vulnerable populations.

Machine learning processing and techniques similar to those discussed above in connection with the method 700 are discussed in greater detail in the aforementioned U.S. patent application Ser. No. 16/801,722, entitled "MACHINE LEARNING TECHNIQUES FOR IMPROVED WATER SERVICE DELIVERY" and filed on Feb. 26, 2020.

All of the disclosed methods and procedures described in this disclosure can be implemented using one or more computer programs or components. These components may be provided as a series of computer instructions on any conventional computer readable medium or machine readable medium, including volatile and non-volatile memory, such as RAM, ROM, flash memory, magnetic or optical disks, optical memory, or other storage media. The instructions may be provided as software or firmware, and may be implemented in whole or in part in hardware components such as application-specific integrated circuits (ASICs), field programmable gate arrays (FPGAs), digital signal processors (DSPs) or any other similar devices. The instructions may be configured to be executed by one or more processors, which when executing the series of computer instructions, performs or facilitates the performance of all or part of the disclosed methods and procedures.

EXAMPLES

Figure 3:
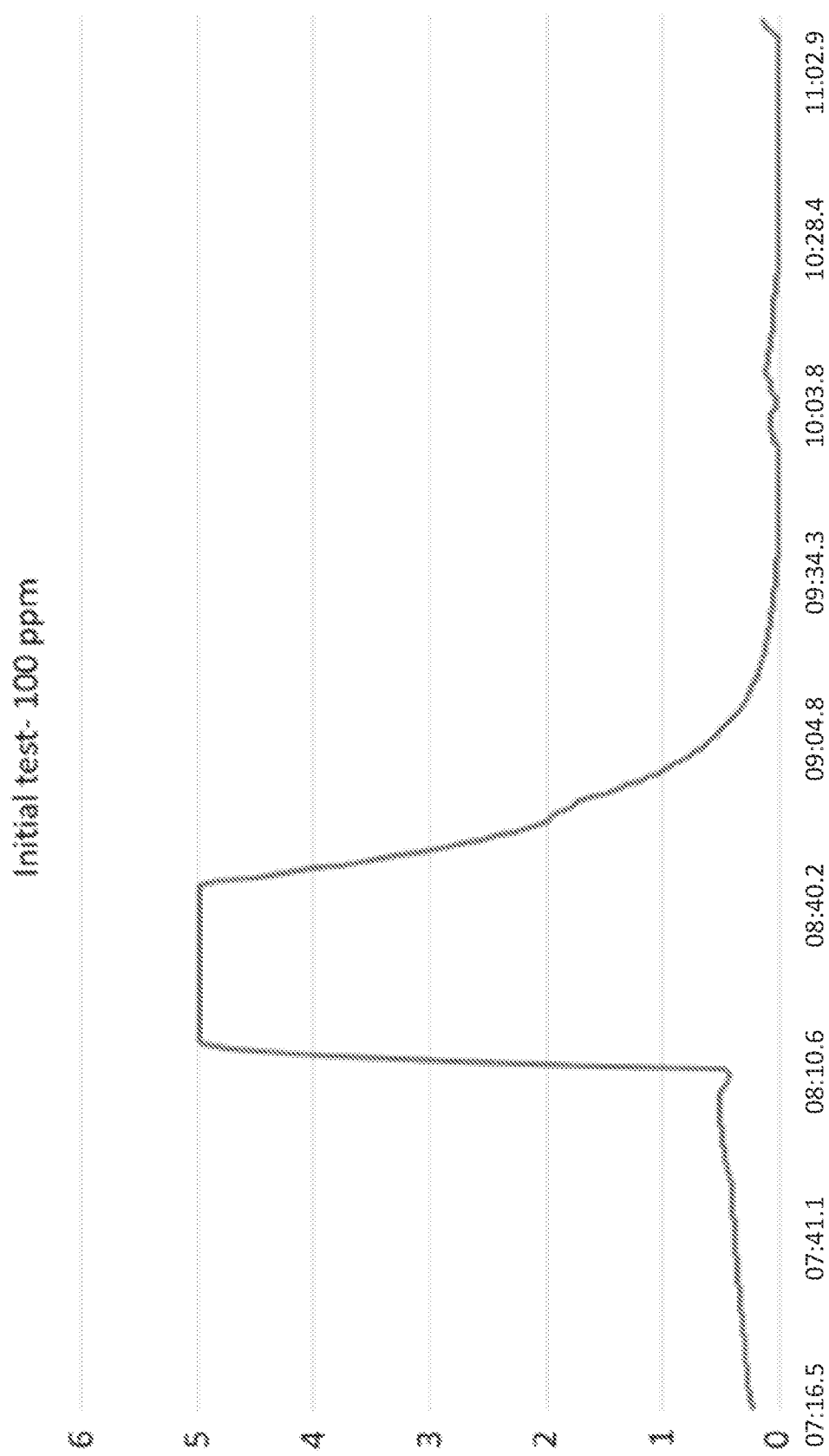
FIG. 3 illustrates an example response from an exemplary embodiment of the present disclosure when challenged with 100 ppm tryptophan.

In an embodiment, a sensor of the present disclosure was challenged using tryptophan solutions ranging from 1 ppb up to 100 ppm. As shown in FIG. 3, when challenged with 100 ppm tryptophan, the fluorimeter clearly and strongly detected the contaminant.

Figure 5:
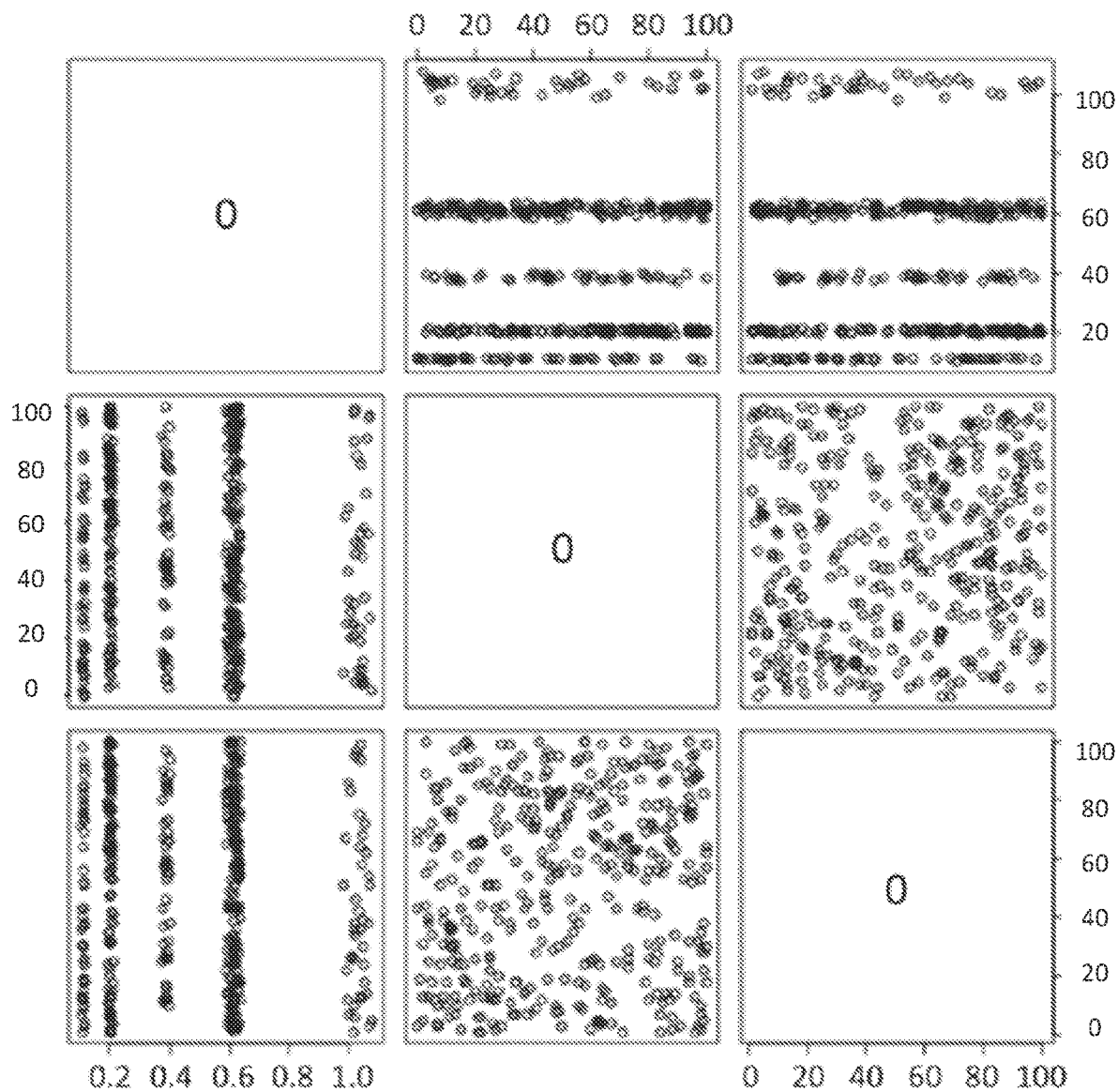
FIG. 5 illustrates a classifying system according to an exemplary embodiment of the present disclosure.

As further shown in FIG. 4, even contamination levels as low as 1 ppb TLF were able to be detected. As also shown in FIG. 5, as 1 ppb TLF is defined as a "high risk" microbial contamination, such a detection is significant.

In an embodiment, an algorithm was created to distinguish between signal and noise despite changes in background signal and aging optical and electronics support. The algorithm used a classification system that considered local rainfall, day of week, and previous system performance to then identify the probability of a "high risk" contamination event.

Figure 6:
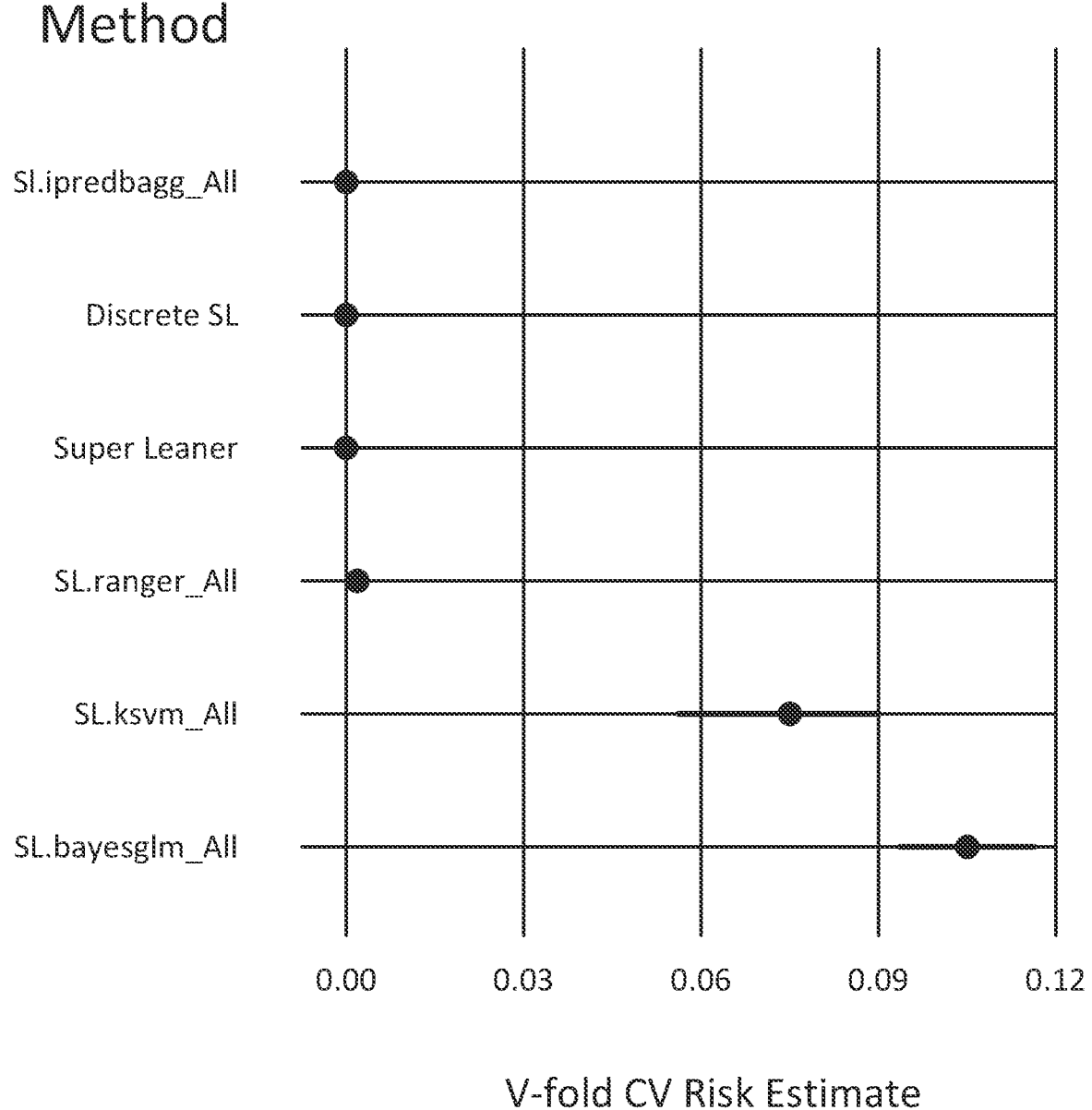
FIG. 6 illustrates experimental classifier output according to an exemplary embodiment of the present disclosure.

As shown in FIG. 6, a training set to meet the criteria for "high risk" contamination was used to yield 100% accuracy and prediction rate for contamination events.

| Confusion Matrix and Statistics |
|---|
| Reference |
| Prediction 0 1 |
| 0 46 0 |
| 1 0 336 |
| Accuracy: 1 |
| 95% CI: (0.9904, 1) |
| No Information Rate: 0.8796 |
| P-Value [Acc > NIR]: <2.2e−16 |
| Kappa: 1 |
| Mcnemar's Test P-Value: NA |
| Sensitivity: 1.0000 |
| Specificity: 1.0000 |
| Pos Pred Value: 1.0000 |
| Neg Pred Value: 1.0000 |
| Prevalence: 0.1204 |
| Detection Rate: 0.1204 |
| Detection Prevalence: 0.1204 |
| Balanced Accuracy: 1.0000 |
| 'Positive' Class: 0 |

Figure 8:
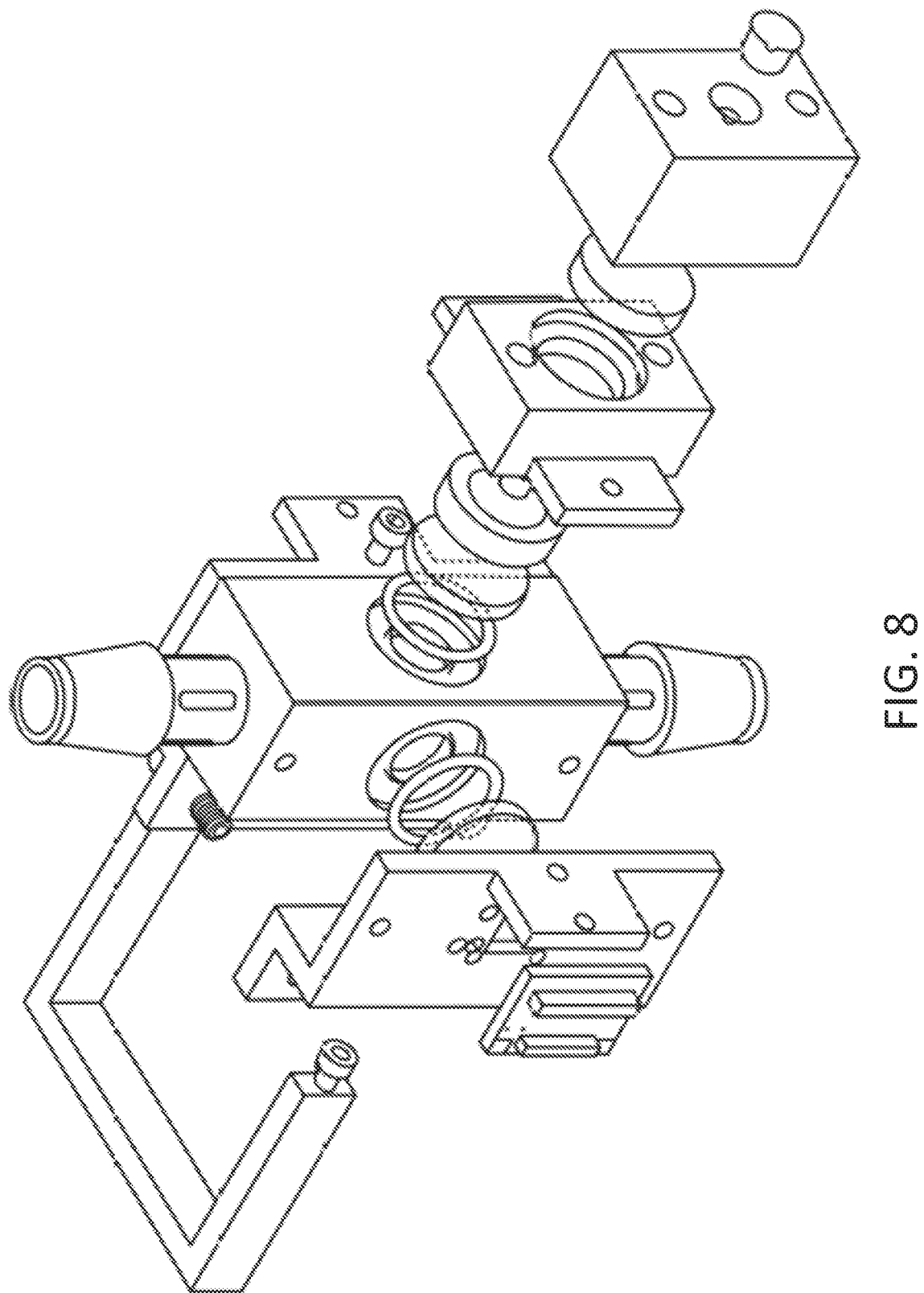
FIG. 8 illustrates a fluorimeter according to an exemplary embodiment of the present disclosure.

In an embodiment, the fluorimeter has the appearance as shown in FIG. 8. The fluorimeter may also be installed with a noise suppressing enclosure as shown in FIGS. 9A and 9B. FIG. 9A illustrates an annotated version of the fluorimeter installed with such noise suppressing enclosure highlighting certain features. FIG. 9B illustrates a non-labeled version of the fluorimeter installed with such noise suppressing enclosure for ease of viewing.

It should be understood that various changes and modifications to the examples described here will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A system comprising:
 a plurality of separate water fixtures, wherein each of the plurality of separate water fixtures includes:
  a light emitting diode centered around an excitation wavelength;
  a bandpass filter;
  a lens;
  a photodiode system; and
  a data transmission system configured to transmit data from each of the plurality of separate water fixtures; and
 a contamination detection system including a microcontroller having a processor and a memory storing instructions, wherein the instructions, when executed by the processor, cause the processor to:
 receive the data from each of the plurality of separate water fixtures;
 calculate changepoints within the data by:
  calculating a first standardized variable for a first segment of the data and a second standardized variable for a second segment of the data;
  determining that a difference between the first and second standardized variables exceeds an optimal threshold; and
  identifying a changepoint between the first segment and the second segment split the data into intervals at the changepoints;
 classify the intervals using a machine learning model; and
 identify a predicted contamination of a water source based on the classified intervals using the data from a subset of the plurality of separate water fixtures.

2. The system of claim 1, wherein the light emitting diode is centered around a tryptophan-like fluorescence excitation wavelength.

3. The system of claim 1, wherein the light emitting diode is centered around an excitation wavelength for an organic contaminant selected from the group consisting of microbes, algaes, fertilizers, resins, phenols, colorants, alcohols, aldehydes, and biowastes.

4. The system of claim 1, wherein each of the plurality of separate water fixtures further includes a picometer.

5. The system of claim 1, wherein each of the plurality of separate water fixtures further includes an enclosure to suppress electromagnetic noise.

6. The system of claim 1, wherein the contamination detection system further comprises:
 a machine learning engine having a training environment configured to train a classifier, wherein the classifier utilizes the machine learning model; and
 an alarm triggered by contamination events, wherein the alarm is calibrated through the machine learning engine.

7. A system for monitoring a microbial level in-situ in a water source, wherein the system comprises:
 a plurality of separate fluorimeters, wherein each of the plurality of separate fluorimeters includes:
  a light emitting diode centered around an excitation wavelength;
  a bandpass filter;

a lens;

a photodiode system; and a data transmission system configured to transmit fluorimeter data from each of the plurality of separate fluorimeters; and a contamination detection system including a microcontroller having a processor and a memory storing instructions, wherein the instructions, when executed by the processor, cause the processor to:

receive the fluorimeter data from each of the plurality of fluorimeters;

calculate changepoints within the fluorimeter data by:

calculating a first standardized variable for a first segment of the fluorimeter data and a second standardized variable for a second segment of the fluorimeter data;

determining that a difference between the first and second standardized variables exceeds an optimal threshold; and identifying a changepoint between the first segment and the second segment split the fluorimeter data into intervals at the changepoints;

classify the intervals using a machine learning model; and identify a predicted contamination of a water source based on the classified intervals using the fluorimeter data from a subset of the plurality of separate fluorimeters.

8. The system of claim 7, wherein each of the plurality of fluorimeters further comprises a picometer.

9. The system of claim 7, wherein each of the plurality of fluorimeters further comprises an enclosure to suppress electromagnetic noise.

10. The system of claim 7, wherein the light emitting diode is centered around a tryptophan-like fluorescence excitation wavelength.

11. The system of claim 7, wherein the light emitting diode is centered around an excitation wavelength for an organic contaminant selected from the group consisting of microbes, algaes, fertilizers, resins, phenols, colorants, alcohols, aldehydes, and biowastes.

12. The system of claim 7, wherein the contamination detection system further comprises:

a machine learning engine having a training environment configured to train a classifier, wherein the classifier utilizes the machine learning model; and an alarm triggered by contamination events, wherein the alarm is calibrated through the machine learning engine.

* * * * *

UNITED STATES PATENT AND TRADEMARK OFFICE
CERTIFICATE OF CORRECTION

| | | |
|---|---|---|
| PATENT NO. | : 11,506,606 B2 | Page 1 of 1 |
| APPLICATION NO. | : 16/804605 | |
| DATED | : November 22, 2022 | |
| INVENTOR(S) | : Emily Bedell et al. | |

It is certified that error appears in the above-identified patent and that said Letters Patent is hereby corrected as shown below:

On the Title Page

Please update the (72) Inventor Section as follows:
(72) Emily Bedell, Denver, CO (US)
Katie Fankhauser, Denver, CO (US)
Taylor Sharpe, Denver, CO (US)
Daniel Wilson, Denver, CO (US)
Evan Thomas, Denver, CO (US)

Signed and Sealed this
Twentieth Day of June, 2023

Katherine Kelly Vidal
*Director of the United States Patent and Trademark Office*